United States Patent [19]

Kramer

[11] 4,395,126
[45] Jul. 26, 1983

[54] APPARATUS FOR REFLECTANCE MEASUREMENT OF FLUORESCENT RADIATION AND COMPOSITE USEFUL THEREIN

[75] Inventor: Donald L. Kramer, Indian Harbor Springs, Fla.

[73] Assignee: Miles Laboratories, Inc., Elkhart, Ind.

[21] Appl. No.: 242,890

[22] Filed: Mar. 12, 1981

[51] Int. Cl.³ ............................................. G01N 21/64
[52] U.S. Cl. .................................. 356/417; 250/228; 250/461.1; 356/236
[58] Field of Search ........... 250/228, 458, 459, 461 R, 250/461 B; 350/1.6, 290; 356/236, 317, 318, 417, 301

[56] References Cited

U.S. PATENT DOCUMENTS

| | | | |
|---|---|---|---|
| 3,516,744 | 6/1970 | Hinman et al. | 356/301 |
| 4,022,529 | 5/1977 | White | 356/318 |
| 4,245,217 | 1/1981 | Steinhage | 350/290 X |
| 4,279,506 | 7/1981 | Maines | 250/458 X |
| 4,306,762 | 12/1981 | Yamashita et al. | 350/290 X |

OTHER PUBLICATIONS

Ware et al., Chemical Physics Letters, vol. 39, No. 3, May 1, 1976, pp. 449–453.

Primary Examiner—F. L. Evans
Attorney, Agent, or Firm—Joseph C. Schwalbach

[57] ABSTRACT

Method and means useful in reflectance measurement is provided wherein radiation of one wavelength is separated from radiation of a different wavelength by the use of a composite of at least two components, one of which is absorptive of said one wavelength radiation and is highly transmissive of said other wavelength radiation, and the other of which is reflective of radiation of both of said wavelengths. The method and means are particularly adapted for use in fluorescent radiation measurement to prevent high intensity residual incident excitation radiation from interfering with measurement of the relatively low intensity fluorescent radiation.

15 Claims, 4 Drawing Figures

APPARATUS FOR REFLECTANCE MEASUREMENT OF FLUORESCENT RADIATION AND COMPOSITE USEFUL THEREIN

BACKGROUND OF THE INVENTION

This invention relates to a method and means for separating radiation of one wavelength from radiation of a different wavelength. In various situations there is need to separate and measure radiation of one wavelength which is mixed with radiation of a different wavelength. One such situation is presented when it is desired to measure infrared radiation which is mixed with radiation in the visible range. A situation in which the invention is particularly useful is presented when it is desired to measure fluorescent radiation which is mixed with residual excitation radiation of a different wavelength.

In the use of conventional fluorescent radiation measurement instrumentation, a fluorescent analyte sample in a cuvette is placed in a beam of monochromatic light, and the resultant absorption of radiant energy by the molecules of the analyte sample raises the vibration level of such molecules from the ground state to one of the excited electronic levels. The absorption step occurs within $10^{-15}$ seconds, and fluorescence results from the spontaneous radiative transition that occurs when the molecules of the analyte sample return to the ground electronic state upon termination of exposure to the incident radiation. The resulting fluorescent light is given off equally in all directions at a wavelength different from that of the exciting light. In terms of intensity measured in photons, the incident light is generally orders of magnitude greater than the emitted fluorescent light, for example of the order of 10,000 to 1 or greater.

In most of the instrumentation available for measurement of fluorescent radiation, the emitted fluorescent radiation is viewed from a direction perpendicular to the incident excitation beam. This geometry minimizes the effect of light scattering by the solution and cell; however, only a very small percentage of the fluorescent light reaches the detector. Since the detector is unable to distinguish between the incident and the fluorescent light, interference filters are used which are intended to prevent residual radiation of the wavelength of the incident beams from reaching the detector, while permitting radiation of the wavelength of the emitted fluorescent radiation to reach the detector.

The need to more effectively collect fluorescent radiation has lead to the development of the so-called integrating sphere-type fluorimeter, such as that shown by W. R. Ware and W. Rothman, in Chem. Phys. Letters 39 (1976) 449. In that instrument the cuvette is located centrally of the integrating sphere and the fluorescent radiation emitted by the sample is reflected by the sphere walls until it is absorbed by a photodetector or lost through the incident beam entrance opening.

While the use of the integrating sphere results in the collection and detection of a substantially greater quantum of fluorescent radiation than was possible with the prior instruments referred to herein, the accuracy of the measurement of such fluorescent radiation is impaired by the fact that, despite the presence of interference filters, interference between residual incident light and the fluorescent light nevertheless occurs. This situation exists because presently available filters are simply unable effectively to screen out all of the residual incident light.

SUMMARY OF THE INVENTION

With the foregoing in mind, it is a general object of the present invention to provide a method and means for separating radiation of one wavelength from radiation of a different wavelength.

It is another object of the present invention to provide a method and means of the class described which are particularly adaptable for use in reflectance measurements which involve the use of a composite of a first component which is highly reflective of radiation of the wavelength to be measured and a second component which is highly transmissive of radiation of the wavelength to be measured and substantially absorptive of radiation of a different interfering wavelength.

Still another object of the present invention is to provide a method and means of the aforementioned character which are particularly well adapted for use in fluorimetric instrumentation of the integrating sphere-type for the separation and absorption of residual excitation radiation and the facilitation of measurement of fluorescent radiation.

A further object of the invention is to provide a composite as aforedescribed which, in one form thereof, the first and second components are dispersed in a substantially non-absorptive vehicle binder, and in another form thereof the first component is a highly reflective substrate surface and the second component is present in a layer superimposed on said reflective surface.

Other and further objects and advantages of the invention will become apparent as the description proceeds, reference being had to the accompanying drawings.

DESCRIPTION OF THE PREFERRED EMBODIMENT

Figure 1:
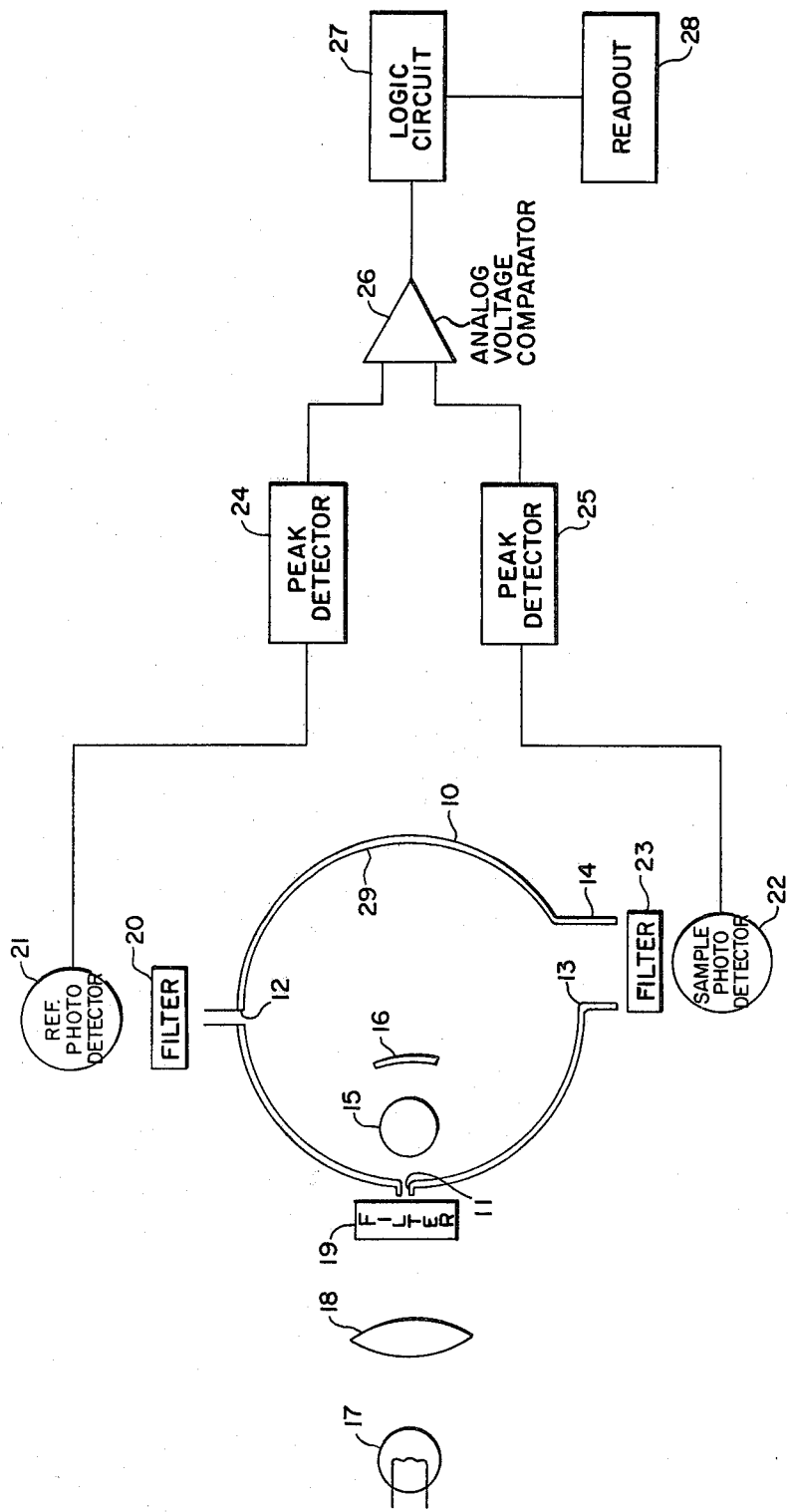
FIG. 1 is a semi-diagrammatic illustration of an integrating sphere-type fluorimeter instrument embodying the invention.

Referring more particularly to FIG. 1 of the drawing, the fluorimeter instrument illustrated therein comprises an integrating sphere 10 formed with a relatively small entrance slit 11 for incident radiation, a relatively small exit slit 12 for reference radiation, and a relatively large exit opening 13 from which a tubular extension 14 projects as shown. A cuvette 15 for accommodating a fluorescent analyte sample is disposed adjacent and radially inwardly of the entrance slit 11, and disposed radially inwardly and adjacent the cuvette 15 is a concave mirror 16.

Means is provided for directing incident high intensity radiation from a source 17 through the entrance slit 11 and through cuvette 15. The source 17 preferably takes the form of a short arc xenon flash lamp capable of producing a short, e.g. $10^{-8}$ seconds, very intense flash of light. A lamp found satisfactory for this purpose is the FX 332 lamp made by the Electro-Optics Division of E.G. & G. Inc., 35 Congress Street, Salem, Mass. Disposed between the source 17 and entrance slit 11 are a condenser lens 18 and a narrow bandpass interference filter 19. The purpose of the condenser lens 18 is to focus the light from the arc of lamp 17 through the filter 19 and slit 11 to the cuvette 15. The purpose of the filter 19 is to limit to a particular wavelength, for example 400 nm, the excitation radiation which enters the entrance slit and illuminates the sample in cuvette 15.

Disposed outwardly adjacent the reference radiation slit 12 is a reference photodetector 21, and interposed between the photodetector 21 and the slit 12 is a narrow bandpass interference filter 20 which is similar to the filter 19 and limits the radiation which can reach the photodetector 21 to the same wavelength as that which is permitted to enter the entrance slit 11.

Disposed outwardly adjacent the tubular extension 14 is a sample photodetector 22, and interposed between the extension 14 and photodetector 22 is a narrow bandpass interference filter 23. The purpose of the filter 23 is to limit the radiation which can reach the sample photodetector 22 to radiation of the wavelength emitted by the particular fluorescent analyte in the cuvette 15, plus or minus about 10 nm.

The electronic circuitry for the illustrated fluorimeter includes peak detectors 24 and 25 connected respectively to the reference photodetector 21 and sample photodetector 22, said photodetectors in turn, being connected to an analog voltage comparator 26. The comparator 26 is connected to appropriate logic circuitry 27, to which is connected readout or display means 28.

In operation of the instrument of FIG. 1 thus far described, the lamp 17 produces a very intense flash of light of short duration, i.e. $10^{-8}$ seconds. Lens 18 focuses the light from the lamp through the filter 19 and entrance slit 11 to and through the cuvette 15 and the analyte contained therein. After passing through the cuvette 15, the light strikes the mirror 16 which focuses the light back through the cuvette and analyte contained therein and toward the opening 11, thereby illuminating the analyte sample twice with each flash. Absorption of this radiant energy by the molecules of the analyte sample raises the vibrational level of such molecules from the ground state to one of the excited electronic levels. The absorption step occurs within $10^{-15}$ seconds, and fluorescence results from the spontaneous radiative transition that occurs when the molecules of the analyte sample return to the ground electronic state upon cessation of the flash of incident radiation. The resulting fluorescent light is given off equally in all directions at a wavelength different from that of the exciting light, and the intensity of the fluorescent emission is indicative of the sample being analyzed.

The optimum excitation radiation wavelength and the wavelength of the resultant fluorescent emission varies for different fluorescent analyte sample materials (fluorophores). Table 1 lists such wavelengths for several common fluorophores.

TABLE 1

| Fluorophore | Excitation Wavelength (nm) | Fluorescent Emission Wavelength (nm) |
|---|---|---|
| Tryptophan | 275 | 348 |

TABLE 1-continued

| Fluorophore | Excitation Wavelength (nm) | Fluorescent Emission Wavelength (nm) |
|---|---|---|
| 1-Naphthol | 335 | 455 |
| NADH | 340 | 435 |
| Quinine | 350 | 450 |
| Umbelliferone | 365 | 450 |
| Umbelliferone-3-Carboxamide | 405 | 450 |
| Acridine | 450 | 530 |
| Riboflavin | 455 | 525 |
| Fluorescein | 480 | 520 |
| Resorufin | 540 | 580 |
| Rhodamine B | 550 | 605 |

Figure 2:
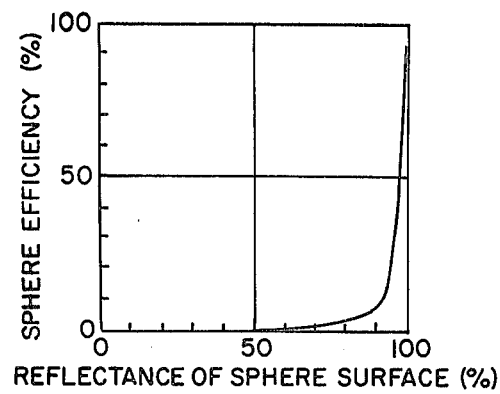
FIG. 2 is a graphic illustration of the general relationship between the efficiency and the reflectance of an integrating sphere.

The fluorescent radiation emitted by the analyte in the cuvette 15 is reflected by the sphere walls until it passes out the opening 13 and is absorbed by the photo detector 22 or is lost through the slits 11 or 12. The efficiency of the sphere in accomplishing reflection of the fluorescent radiation is a function of the sphere surface reflectance and is illustrated generally by the curve shown in FIG. 2.

One of the major problems presented in operation of instrumentation of the type thus far described is interference between residual incident light and the fluorescent light emitted from the analyte sample. This situation exists because presently available filters, while providing maximum blocking to wavelengths outside the bandpass of the filter, do not completely block wavelengths outside the bandpass thereof. Moreover, the photodetector 22 is responsive to a relatively wide range of radiation wavelengths. Thus, filter 23 is unable to block all residual incident light from reaching and being detected by the photodetector 22.

The present invention prevents such residual incident radiation from interfering with the measurement of the fluorescent radiation by providing means for absorption of said incident radiation within the sphere 10. Such absorption is provided by the use in the sphere 10 of a composite which, in the presently preferred form of the invention, is a layer 29 which is superimposed on the inner surface of the sphere 10. Layer 29 comprises a first component reflective of both the incident residual radiation and of the fluorescent radiation, and a second component which is highly transmissive of fluorescent radiation but is absorptive of residual incident radiation.

Since, as shown in Table 1, the wavelength of the fluorescent radiation is different from that of the excitation radiation, the preferred material for the second component is a filter glass which is highly transmissive of the fluorescent radiation wavelength and is absorptive of the incident radiation wavelength. A suitable highly reflective first component substance is barium sulfate, and it is preferred that both the first and the second component be present in a finely divided state and dispersed within a substantially non-absorptive vehicle binder similar to that used in paint.

Filter glass is available from a number of manufacturers, including Corning Glass Works, Corning, New York and Schott Optical Glass, Duryea, Pennsylvania. The composite may be made by grinding the appropriate filter glass to a powder and dispersing it in a barium sulfate paint, such as Eastman 6080 White Reflectance Coating, available from PBL Electro Optics, New London, N.H. The resulting paint-like mixture is applied as a paint to the inner surface of the sphere 10 and is allowed to cure.

Figure 4:
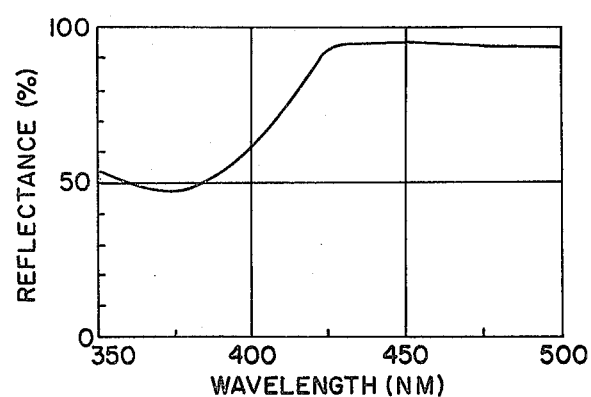
FIG. 4 is a graphic illustration of the approximate spectral reflectance characteristics of a coating material of the type used in the practice of the invention.

FIG. 4 illustrates spectral reflectance characteristics of a composite produced from such a paint-like mixture in which barium sulfate and GG420 filter glass are present in a 1:1 ratio by weight. It will be observed that the composite is poorly reflective, i.e. substantially absorptive, of radiation of a wavelength of about 375 nm and is highly reflective of radiation having a wavelength of 435 nm and above. With reference to Table 1, it will be apparent that such a composite can be advantageously used in the present invention to separate residual incident radiation from fluorescent radiation in the measurement of the fluorescent radiation from the fluorophores quinine or umbelliferone.

The fluorescent radiation emitted by the sample is reflected by the composite on the sphere walls until it is absorbed by the large area photodetector 22 or escapes through the openings 11 or 12. However, most of the incident radiation is lost through absorption during multiple reflection thereof within the sphere 10. Part of the incident radiation is absorbed each time it impinges upon an area of the composite 29, and the portion thereof which is not absorbed is reflected to another area of the composite 29 where another portion thereof is absorbed, the remaining portion being reflected to still another area of the composite 29. Such absorption/reflection continues until most of the incident radiation is absorbed, the remainder being prevented from reaching the photodetector 22 by filter 23.

The composite 29 exhibits poor light reflectance at the excitation wavelength and high reflectance at the fluorescent wavelength of the particular fluorophore for which the analyte sample is tested. The ground filter glass in the composite is selected for its ability to attenuate the particular exciting wavelength for the fluorophore in the analyte, to effect absorption and hence reduce transmittance thereof. Barium sulfate, on the other hand, exhibits a high degree of reflectance of both the excitation and the fluorescent wavelengths. In a composite of barium sulfate and ground glass in a paint-like nonabsorptive vehicle binder, made as aforedescribed, the barium sulfate and filter glass may be present in a range by weight of from about 5:1 to about 1:2 of barium sulfate to filter glass, the preferred ratio being the aforementioned 1:1 ratio of barium sulfate to filter glass.

Figure 3:
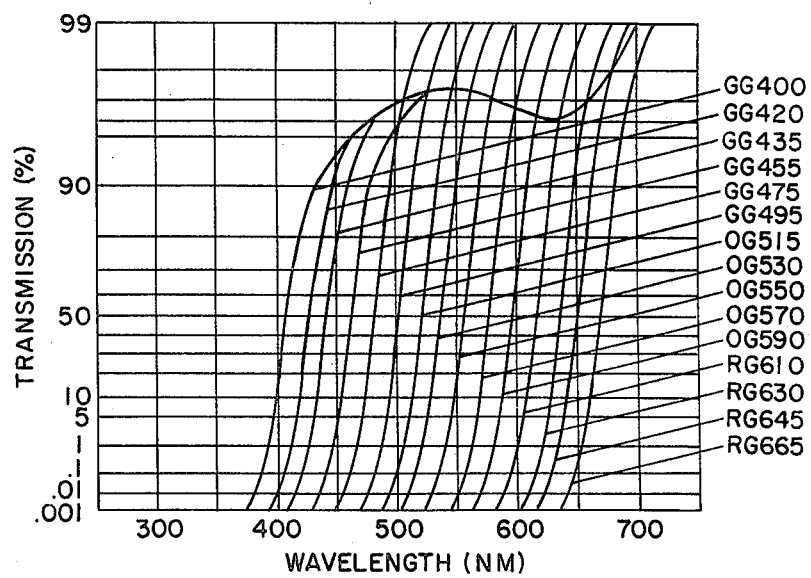
FIG. 3 is a graphic illustration of the percent transmission at various wavelengths of a number of filter glasses.

FIG. 3 illustrates the percent light transmission at various wavelengths of a number of commercially available glasses commonly used in "cut-off" filters and which are of the type which is useful in the present invention. The particular glass selected depends upon the wavelength of the incident radiation and the fluorescent emission from the particular analyte to be tested, it being understood that a given composite is chosen to optimize the measurement of fluorescence from a particular analyte. For example, in the cases where an analyte is to be tested for quinine or umbelliferone, each of which exhibits fluorescent emission of 450 nm responsive to excitation of about 350 nm, FIG. 3 shows that GG 420 (green glass exhibiting 50% transmission at 420 nm) provides the desirable characteristics of about 92% transmission at 450 nm and about 0.001% transmission at about 390 nm.

It is not uncommon for fluorescent analytes to yield more than one wavelength of fluorescent radiation. In such a case, in order to measure all of the fluorescent radiation, to the exclusion of residual incident radiation, the composite can include one glass chosen for its high transmission at one fluorescent wavelength and another glass chosen for its high transmission at the other fluorescent wavelength, both glasses being poorly transmissive at the wavelength of the residual excitation radiation.

While the invention as presently preferred utilizes a composite of components in the form of the coating which includes barium sulfate and one or more selected filter glasses in finely divided form in a nonabsorptive vehicle binder such as that used in the aforementioned Eastman 6080 White Reflectance Coating, the invention also contemplates a number of modified forms. One such modified form utilizes as the highly reflective component in the coating 29 a finely divided fluorocarbon polymer, rather than barium sulfate. One such polymer which is satisfactory for this purpose is that sold under the trademark HALON® by E. I. duPont DeNemours and Company, Wilmington, Delaware.

Another form of the invention utilizes as the highly reflective component a material such as titanium dioxide or magnesium oxide.

The highly reflective component of the composite may also take the form of a highly reflective finish, for example a suitable metallic mirror finish, on the inner surface of the integrating sphere 10, which surface is overlaid with a coating of the selected ground filter glass component in a nonabsorptive vehicle binder. Exemplary of such a coating is the coating 29 of FIG. 1 which contains ground filter glass, but which does not contain barium sulfate.

In still another form of the invention, the highly reflective composite component takes the form of a highly reflective finish on the inner surface of the sphere 10, and the selected filter glass takes the form of a continuous solid layer superimposed on the highly reflective finish and having a diffuse exposed surface. This filter layer may be applied directly to the highly reflective finish, or it may take the form of a replaceable globe of filter glass which fits within the sphere 10 and overlays the highly reflective surface. Such replaceable globes afford the instrument versatility in use, permitting the measurement of fluorescent emission from a variety of analytes by virtue of the availability of globes having transmittance characteristics appropriate, respectively, to the measurement of fluorescence emitted by a number of different fluorophores.

By the expression "highly reflective finish" it is intended to include, not only suitable highly polished metallic surfaces, but also other surfaces which are highly reflective of both the fluorescent and the incident radiation wavelengths. Such a surface may, for example, be one to which highly reflective characteristics are imparted by an applied layer of highly reflective paint, such as the Eastman 6080 White Reflectance Coating mentioned hereinbefore.

Various other changes and modifications may be made without departing from the spirit of the invention, and all such changes are contemplated as may come within the scope of the appended claims.

What is claimed as the invention is:

1. Apparatus useful in reflectance measurement of fluorescent radiation emitted by an analyte during transition thereof from an excited state to a ground state, comprising an integrating sphere within which an analyte can be subjected to incident radiation effective to raise such analyte to an excited state, the inner surface of said integrating sphere comprising a composite of two components, at least one of which is in a finely divided state, is dispersed in a vehicle binder which is substantially nonabsorptive of radiation, is transmissive of fluorescent radiation, and is absorptive of incident radiation; and the other component is reflective of both incident and fluorescent radiation.

2. Apparatus as in claim 1 wherein said at least one component is filter glass.

3. Apparatus as in claim 1 wherein said at least one component is filter glass, and the other component is a reflective inner surface of said integrating sphere on which said vehicle binder is superimposed.

4. Apparatus as in claim 1 wherein both of said components are in a finely divided state and are dispersed in said vehicle binder.

5. Apparatus as in claim 1 wherein said at least one component is filter glass, and the other component is also in a finely divided state and dispersed in said vehicle binder.

6. A composite useful for the separation of radiation of one wavelength from radiation of another different wavelength, comprising two components in a finely divided state dispersed in a vehicle binder which is substantially nonabsorptive of radiation of either of said wavelengths, one of said components being transmissive of radiation of said one wavelength and absorptive of radiation of said other wavelength, and the other component being reflective of radiation of both of said wavelengths.

7. The composite of claim 6 wherein the radiation of which said one component is transmissive is fluorescent radiation emitted by a fluorescent analyte during the transition thereof from an excited state to a ground state, and the radiation of which the first component is absorptive is incident excitation radiation effective to raise such an analyte to the excited state, and the other component is reflective of both said incident and said fluorescent radiation.

8. The composite of claim 6 wherein said one component is filter glass transmissive of fluorescent radiation emitted by a fluorescent analyte during the transition thereof from an excited state to a ground state and is absorptive of incident radiation effective to raise such an analyte to the excited state, and the other component is selected from the group consisting of barium sulfate, a highly reflective fluorocarbon polymer, titanium dioxide and magnesium oxide, said other component being reflective of both said incident and said fluorescent radiation.

9. Apparatus useful in reflectance measurement of fluorescent radiation emitted by an analyte during transition thereof from an excited state to a ground state, comprising an integrating sphere having an opening therein; a cuvette within said sphere adjacent said opening; means for directing incident radiation from an external source through said opening toward and through said cuvette; and a focusing mirror in said sphere on the side of the cuvette opposite said opening positioned to reflect back through the cuvette and towards said opening incident radiation which has passed through the cuvette, the inner surface of the integrating sphere comprising a composite of a first component transmissive of fluorescent radiation and absorptive of incident radiation, and a second component reflective of both fluorescent and incident radiation.

10. Apparatus as in claim 9 wherein the first component of said composite is filter glass.

11. Apparatus as in claim 9 wherein the two components of the composite are in a finely divided state dispersed in a vehicle binder which is substantially nonabsorptive of radiation, and said first component is filter glass.

12. Apparatus as in claim 9 wherein the first component of said composite is a layer of filter glass, and the second component is a reflective surface on which the layer of filter glass is superimposed.

13. Apparatus useful in reflectance measurement of fluorescent radiation emitted by an analyte during transition thereof from an excited state to a ground state, comprising an integrating sphere within which an analyte can be subjected to incident radiation effective to raise such analyte to an excited state, the inner surface of said integrating sphere comprising a composite of two components, one of which is transmissive of fluorescent radiation and is absorptive of incident radiation, and the other of which is reflective of both incident and fluorescent radiation.

14. Apparatus as in claim 13 wherein said one component is filter glass.

15. Apparatus as in claim 13 wherein said one component is a layer of filter glass, and the other component is a reflective inner surface of said integrating sphere on which said filter glass layer is superimposed.

* * * * *